United States Patent
Vyas et al.

(10) Patent No.: US 10,891,311 B2
(45) Date of Patent: Jan. 12, 2021

(54) METHOD FOR GENERATING SYNTHETIC DATA SETS AT SCALE WITH NON-REDUNDANT PARTITIONING

(71) Applicant: Red Hat, Inc., Raleigh, NC (US)

(72) Inventors: Jay Vyas, Concord, MA (US); Ronald Nowling, West Allis, WI (US); Huamin Chen, Westborough, MA (US)

(73) Assignee: RED HAT, INC., Raleigh, NC (US)

( * ) Notice: Subject to any disclaimer, the term of this patent is extended or adjusted under 35 U.S.C. 154(b) by 988 days.

(21) Appl. No.: 15/294,142

(22) Filed: Oct. 14, 2016

(65) Prior Publication Data
US 2018/0107729 A1    Apr. 19, 2018

(51) Int. Cl.
| | | |
|---|---|---|
| G06F 16/28 | (2019.01) | |
| G06N 20/00 | (2019.01) | |
| G16H 10/60 | (2018.01) | |
| G16H 50/70 | (2018.01) | |
| G06N 7/00 | (2006.01) | |

(52) U.S. Cl.
CPC .......... *G06F 16/285* (2019.01); *G06N 7/005* (2013.01); *G06N 20/00* (2019.01); *G16H 10/60* (2018.01); *G16H 50/70* (2018.01)

(58) Field of Classification Search
CPC ...... G06F 16/285; G06N 20/00; G06N 7/005; G16H 10/60; G16H 50/70
See application file for complete search history.

(56) References Cited

U.S. PATENT DOCUMENTS

| | | | |
|---|---|---|---|
| 6,032,216 A | 2/2000 | Schmuck et al. | |
| 7,433,820 B2 | 10/2008 | Garg et al. | |
| 8,065,244 B2 | 11/2011 | Chen et al. | |
| 8,122,108 B2 | 2/2012 | Revanuru et al. | |
| 8,374,974 B2 | 2/2013 | Chen et al. | |
| 8,805,861 B2 | 8/2014 | Boyan et al. | |
| 8,935,167 B2 | 1/2015 | Bellegarda | |
| 9,076,108 B2 | 7/2015 | Frank et al. | |
| 10,423,890 B1* | 9/2019 | Fogarty | G06N 5/047 |
| 2007/0094061 A1 | 4/2007 | Hu et al. | |

(Continued)

OTHER PUBLICATIONS

Page, John, "The role of solar-radiation climatology in the design of photovoltaic systems," Practical Handbook of Photovoltaics, Academic Press, 2012. (Year: 2012).*

(Continued)

*Primary Examiner* — Jay A Morrison
(74) *Attorney, Agent, or Firm* — K&L Gates LLP

(57) ABSTRACT

An example system includes a first machine and a second machine, a clustering module, and a training module. The clustering module receives a plurality of data sets, each including attributes. The clustering module partitions the plurality of data sets into a first clustered data set and a second clustered data set. Each data set of the plurality of data sets is partitioned. The training module assigns a first stochastic model to the first clustered data set and a second stochastic model to the second clustered data set. The first machine selects the first clustered data set and the first stochastic model and generates a first synthetic data set having generated data for each one of the attributes. The second machine selects the second clustered data set and the second stochastic model and generates a second synthetic data set having generated data for each one of the attributes.

19 Claims, 7 Drawing Sheets

(56) References Cited

U.S. PATENT DOCUMENTS

| | | | | |
|---|---|---|---|---|
| 2007/0265811 A1* | 11/2007 | Chalasani | ............... | G06Q 10/04 703/2 |
| 2008/0294941 A1* | 11/2008 | Copstein | ............. | G06F 11/3684 714/38.1 |
| 2009/0099779 A1* | 4/2009 | Bouzas | .................... | G01V 1/28 702/17 |
| 2012/0065961 A1 | 3/2012 | Latorre et al. | | |
| 2012/0197884 A1* | 8/2012 | Duan | ................. | G06F 11/3684 707/736 |
| 2012/0323829 A1* | 12/2012 | Stokes | ................. | G06K 9/6224 706/12 |
| 2013/0297276 A1* | 11/2013 | Imai | ....................... | G16C 99/00 703/12 |
| 2014/0143186 A1 | 5/2014 | Bala | | |
| 2014/0280142 A1* | 9/2014 | Wasson | ............... | G06F 16/2465 707/737 |
| 2014/0372348 A1* | 12/2014 | Lehmann | ................. | G06N 5/04 706/12 |
| 2015/0121370 A1* | 4/2015 | Beisiegel | ............ | G06F 9/45558 718/1 |
| 2015/0278317 A1* | 10/2015 | Dygas | ................... | G06F 16/283 707/602 |
| 2016/0196374 A1* | 7/2016 | Bar | ........................ | G06F 17/18 703/2 |
| 2017/0061286 A1* | 3/2017 | Kumar | ............... | G06Q 30/0269 |
| 2018/0247226 A1* | 8/2018 | Forman | ................ | G06K 9/6262 |

OTHER PUBLICATIONS

Zhang et al., Computational Web Intelligence: Intelligent Technology for Web Applications, 2004, pp. 124-128.
Li et al., Building a Decision Cluster Classification Model for High Dimensional Data by a Variable Weighting k-Means Method, AI 2008: Advances in Artificial Intelligence, Lecture Notes in Computer Science, 2008, pp. 337-347.
Stocca, Juan, Markov Mixture Models, Nov. 23, 2015 (12 pages).
Markov text generators, Wikipedia, https://en.wikipedia.org/wiki/Markov_chain#Markov_text_generators.
Nowling et al., A Domain-Driven, Generative Data Model for BigPetStore, 2014 IEEE Fourth International Conference on Big Data and Cloud Computing, pp. 49-55.

* cited by examiner

METHOD FOR GENERATING SYNTHETIC DATA SETS AT SCALE WITH NON-REDUNDANT PARTITIONING

BACKGROUND

Modern technology often involves a great deal of information and data, thus necessitating information management in one form or another. Improvements to information management and related technologies are typically implemented by management applications, databases, etc. Though applications and databases may improve management of information, the applications and databases must often be tested (e.g., with sample data) prior to implementation in active systems.

One typical example of information management is a hospital network, managing thousands of individual health records. To implement a new application or database into this network, the application or database should first be tested. However, particularly in the health record space, active data records may be unavailable for testing purposes. For example, a developer creating an application for a hospital may not have a sufficient quantity of records to fully test the capabilities or limits of the application or database (e.g., memory limitations, processing limitations, garbage collection limitations, etc.). Furthermore, active records may be confidential (e.g., because of healthcare or hospital policies) and thus cannot be directly used for testing purposes.

SUMMARY

The present disclosure provides a new and innovative method and system for generating synthetic data sets at scale with non-redundant partitioning. For example, the method includes receiving, by a clustering module, a plurality of data sets. Each data set of the plurality of data sets includes a plurality of attributes. The clustering module partitions the plurality of data sets into a plurality of clustered data sets including at least a first clustered data set and a second clustered data set. Each data set of the plurality of data sets is partitioned into one of the plurality of clustered data sets. The method includes assigning, by a training module, a respective stochastic model to each respective clustered data set of the plurality of clustered data sets. This includes assigning a first stochastic model to the first clustered data set, and assigning a second stochastic model to the second clustered data set. The method includes selecting, by a first machine, the first clustered data set and the first stochastic model. The method further includes selecting, by a second machine, the second clustered data set and the second stochastic model. The first machine generates, with the first stochastic model, a first synthetic data set. The first synthetic data set has generated data for each one of the plurality of attributes. The second machine generates, with the second stochastic model, a second synthetic data set. The second synthetic data set has generated data for each one of the plurality of attributes.

Additional features and advantages of the disclosed method and system are described in, and will be apparent from, the following Detailed Description and the Figures.

DETAILED DESCRIPTION OF EXAMPLE EMBODIMENTS

Figure 1:
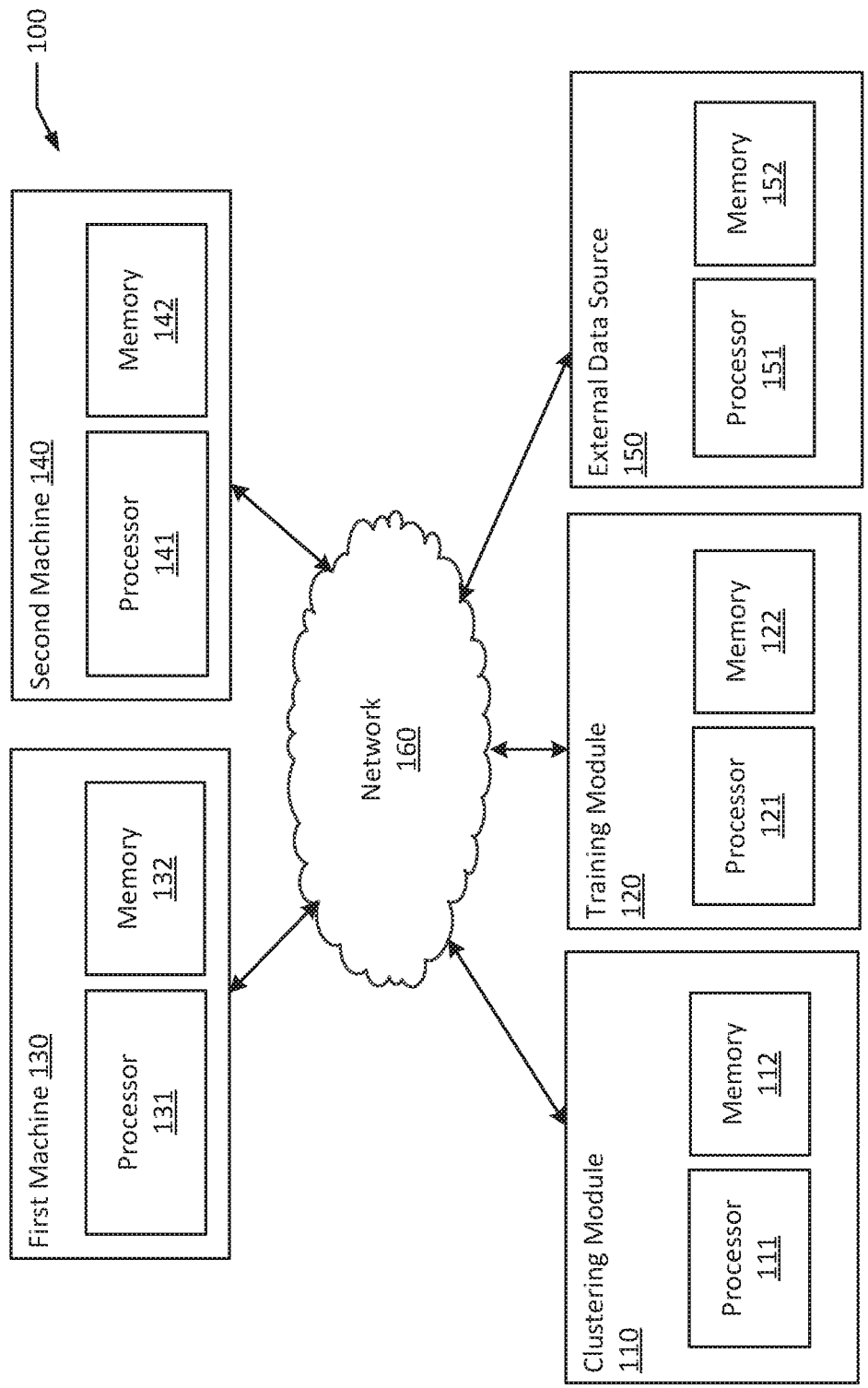
FIG. 1 is a block diagram of an exemplary system for generating synthetic data sets according to an example embodiment of the present disclosure.

Generation of synthetic data allows for creation of large data sets that are used for effective testing of applications, databases, etc. Typically, random data generation is implemented to generate synthetic data; however, for example, using random text or numeric data for synthetic data has drawbacks.

Generally, random data does not properly test indexing algorithms (e.g., algorithms that have unique scaling constraints) Likewise, random data does not result in queries or load profiles that may trigger all unique aspects of an application. For example, randomly generated data will often result in statistical distributions that are random. In this sense, the randomly generated data does not represent real-world identities, trends, etc. Additionally, random data generation may result in intersecting data or redundant records (e.g., duplicates). To eliminate redundancy, generated data may require additional processing or filtering. This is typically required with randomly generated data that is not seeded against unique inputs. While redundant records may be filtered, filtering large amounts of data is a source of computing inefficiency.

Redundancy may be avoided by using a unique seed for each and every data generator. However, unique seeding often leads to other problems. For example, different data generators will all generate roughly similar distributions of synthetic data, varying only in the terms of random identity. Because of this, different data generators will not generate synthetic data that is truly representative of an individual cluster of real clients, so the synthetic data is not representative of real world data.

Additionally, while a single machine (e.g., a single computer) may be used to generate synthetic data, particular circumstances often require that test data is synthetically generated by multiple parallel systems (e.g., two or more machines generating synthetic data) to save time, optimize computing resources, etc. When this is the case, it is preferable that the multiple parallel systems are generating unique sets of data (e.g., avoiding data intersection). Additionally, in distributed computing environments, the need to simulate chaotic load from large number of light clients, which may represent different real world groupings, does not match impedance with a single data generator model. Therefore, multiple parallel machines in one or more parts of a distributed system are often desired.

The problem remains of how to develop a data synthesizing system that can generate large amounts of unique synthetic data, at scale, which has some intuitive mapping to a sample data set from the real world and the synthetic data is generated as if it were non-synthetic data from individual domains, regions, demographics, or other naturally existing, real-world distinctions for load generation. Existing solutions include multiple parallel systems generating the same class of synthetic data at the same time, but this means the data may be redundantly generated, resulting in data intersection.

The systems and methods disclosed herein address the problems discussed above. For example, the system allows for parallel synthetic data generation by multiple machines. A clustering module receives data sets and partitions the data sets into non-redundant clusters. A training module assigns a respective stochastic model to each clustered data set. Each data generating machine may select a different clustered data set and corresponding stochastic model, so each data generating machine generates a different synthetic data set in parallel.

Thus, the present disclosure addresses a specific technological challenge faced by data generating machine systems, or data synthesizers, of generating synthetic data sets at scale that is particularly advantageous for testing applications and databases. The presently disclosed improvements to data synthesizer technology are necessarily rooted in computer technology, requiring a massive amount of information to be dynamically processed and analyzed by parallel computer systems to generate synthetic data that may simulate a real world chaotic load from a large number of light clients.

The presently disclosed system addresses problems in the technological area of synthetic data generation using a specific structure of components, including the clustering module partitioning, which is required to separate sample data into distinct clustered data sets that are assigned to respective stochastic models by the training module. This may advantageously ensure that multiple parallel systems are never generating the same class of data at the same time. For example, locking out individual clustered data sets and stochastic models may ensure that synthetic data may be generated at scale by multiple machines simultaneously and in parallel while avoiding intersection.

FIG. 1 is a block diagram of an exemplary system for generating synthetic data sets according to an example embodiment of the present disclosure. The system 100 includes a clustering module 110, a training module 120, a first machine 130, a second machine 140, and an external data source 150.

Each of the clustering module 110 and the training module 120 may include a processor and a memory. For example, the clustering module 110 includes processor 111 and memory 112. Likewise, for example, the training module 120 includes processor 121 and memory 122. The external data source 150 may also include a processor and a memory. For example, the external data source 150 includes processor 151 and memory 152.

Each of the first machine 130 and the second machine 140 communicate with the clustering module 110 and the training module 120. Also, each of the first machine 130 and the second machine 140 may include a processor and a memory. For example, the first machine 130 includes processor 131 and memory 132. Likewise, for example, the second machine 140 includes processor 141 and memory 142. For example, each of the first machine 130 and the second machine 140 may be a personal computing device, server, virtual machine, or application executing on a personal computing device, server, one or more physical processors, etc. Likewise, for example, each of the first machine 130 and the second machine 140 may be coupled to other processors, other memory devices, and other input/output devices (e.g., a network device, a network interface controller (NIC), a network adapter, any other component that connects a computer to a computer network, a peripheral component interconnect (PCI) device, storage devices, sound or video adaptors, photo/video cameras, printer devices, keyboards, displays, etc.).

Each of the components noted above (e.g., clustering module 110, training module 120, external data source 150, first machine 130, second machine 140, etc.) may be hardwire connected to each other. Additionally, each of the components noted above may be connected to a network 160. For example, the network 160 may be a public network (e.g., the Internet), a private network (e.g., a local area network (LAN) or wide area network (WAN)), or a combination thereof. For example, the first machine 130 and the second machine 140 may communicate with the clustering module 110 and the training module 120 over the network 160 as a distributed system. The system 100 may further include additional machines (e.g., a third machine). In a typical example, dozens, hundreds, or thousands of machines may be executing in parallel in distributed fashion as the system 100 depending on the scale of non-redundant partitioning required by the system 100.

As used herein, a physical processor or processor refers to a device capable of executing instructions encoding arithmetic, logical, and/or I/O operations. In one illustrative example, a processor may follow Von Neumann architectural model and may include an arithmetic logic unit (ALU), a control unit, and a plurality of registers. In a further aspect, a processor may be a single core processor which is typically capable of executing one instruction at a time (or process a single pipeline of instructions), or a multi-core processor which may simultaneously execute multiple instructions. In another aspect, a processor may be implemented as a single integrated circuit, two or more integrated circuits, or may be a component of a multi-chip module (e.g., in which individual microprocessor dies are included in a single integrated circuit package and hence share a single socket). A processor may also be referred to as a central processing unit (CPU).

As discussed herein, a memory device or memory refers to a volatile or non-volatile memory device, such as RAM, ROM, EEPROM, or any other device capable of storing data. As discussed herein, I/O device refers to a device capable of providing an interface between one or more processor pins and an external device capable of inputting and/or outputting binary data. The system 100 can further include a computer readable medium storing instructions, which, when executed cause the clustering module, the training module, the first machine, and the second machine to operate in the ways described herein.

Figure 2A:
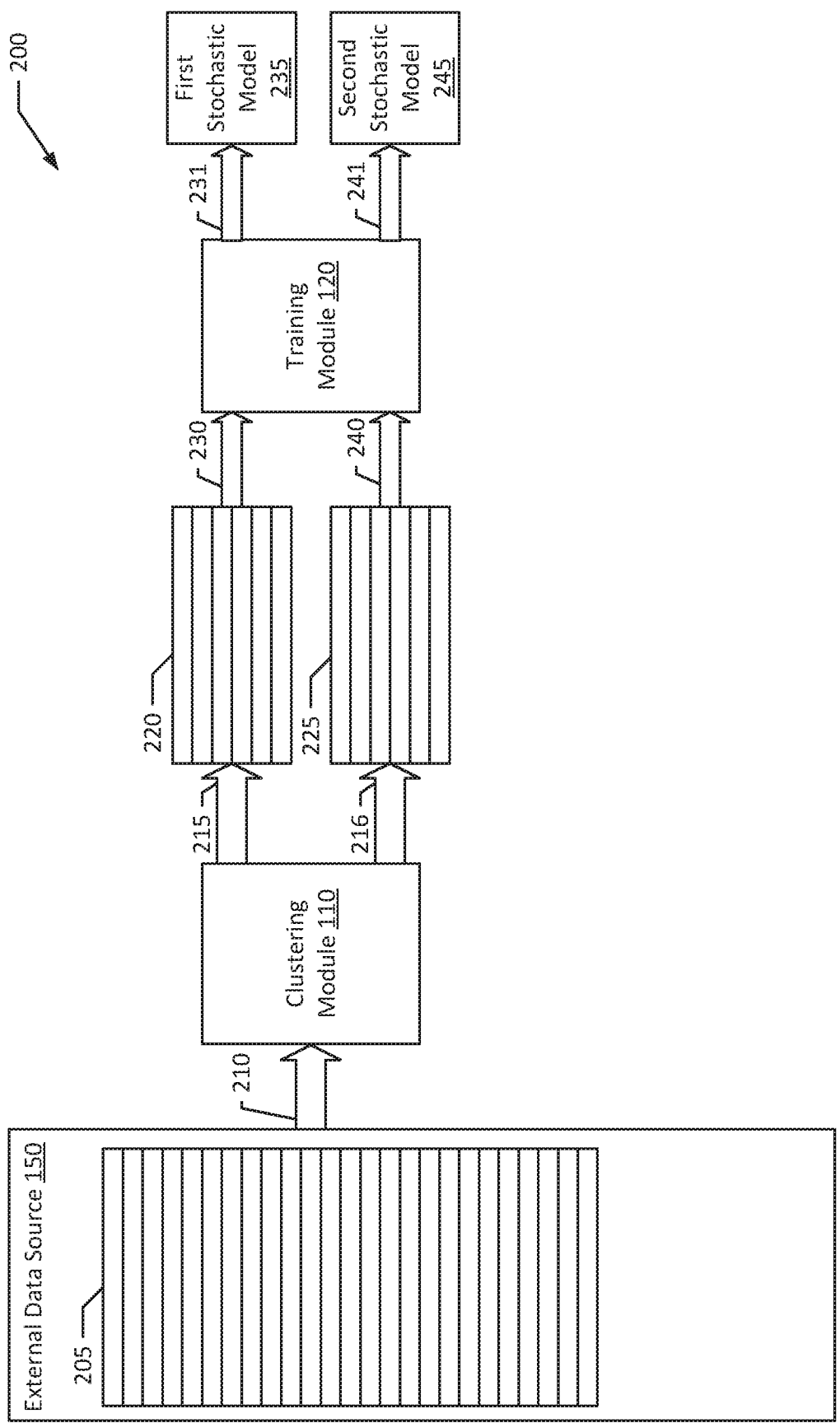
FIGS. 2A-2B are block diagrams of an example method of synthetic data set generation according to an example embodiment of the present disclosure.
Figure 2B:
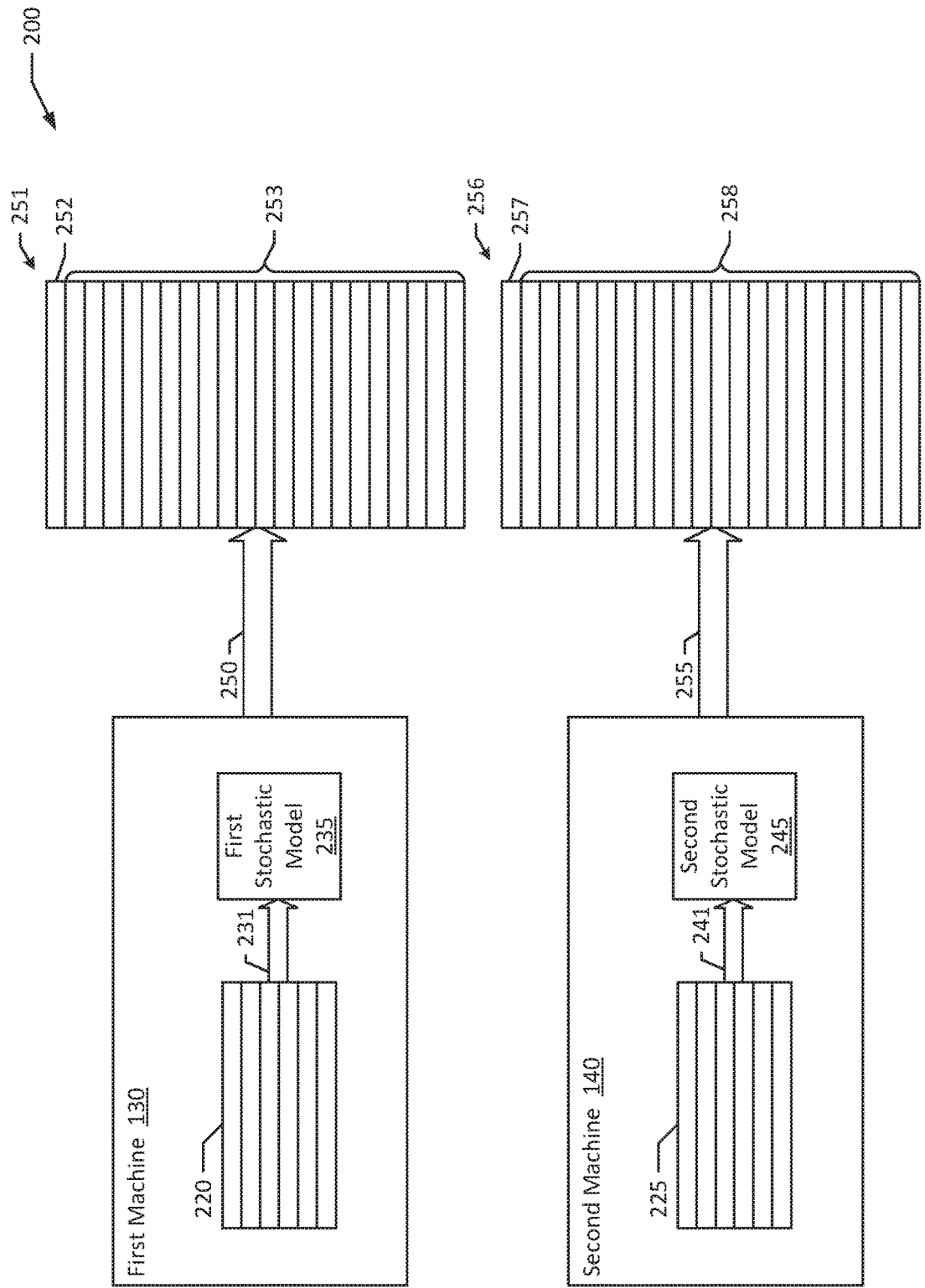

FIGS. 2A-2B are block diagrams of an example method of synthetic data set generation according to an example embodiment of the present disclosure. For example, starting with FIG. 2A, synthetic data generation method 200 may begin with the clustering module 110 receiving a plurality of data sets 205 (e.g., input data) from the external data source 150 (block 210). Each data set of the plurality of data sets 205 includes a plurality of attributes.

The clustering module 110 partitions the plurality of data sets 205 into a plurality of clustered data sets (blocks 215 and 216). For example, the plurality of clustered data sets includes at least a first clustered data set 220 and a second clustered data set 225. Each data set from the plurality of data sets 205 is partitioned into one of the plurality of clustered data sets. For example, as illustrated in FIG. 2A, every data set from the plurality of data sets 205 is partitioned into one of the first clustered data set 220 or the second clustered data set 225. Typically, the clustering module 110 may partition the plurality of data sets 205 into more than two clustered data sets (e.g., ten clustered data sets).

The training module 120 assigns a respective stochastic model to each respective clustered data set of the plurality of clustered data sets. For example, the training module 120 receives the first clustered data set 220 (block 230). The training module 120 assigns a first stochastic model 235 to the first clustered data set 220 (block 231). Likewise, for example, the training module 120 receives the second clustered data set 225 (block 240). The training module 120 assigns a second stochastic model 245 to the second clustered data set 225 (block 241). In a different example, the training module 120 assigns the second stochastic model 245 to the first clustered data set 220; likewise, the training module 120 assigns the first stochastic model 235 to the second clustered data set 225. In an example, each assignment (e.g., the first stochastic model 235 assigned to the first clustered data set 220) is stored in a data store (e.g., a strongly consistent data store).

Continuing on to FIG. 2B, the first machine 130 selects the first clustered data set 220 and the first stochastic model 235. For example, because the first clustered data set 220 was already assigned to the first stochastic model 235 (block 231), the first machine 130 is only required to select one of the first clustered data set 220 and the first stochastic model 235 to select both since they are paired together. The first machine 130 generates, with the first stochastic model 235, a first synthetic data set 251 (block 250). The first synthetic data set 251 has generated data for each one of the plurality of attributes from the plurality of data sets 205. For example, the first synthetic data set 251 may include a first generated data record 252 and a plurality of additional first generated data records 253. Each of the first generated data record 252 and the plurality of additional first generated data records 253 has each one of the plurality of attributes from the plurality of data sets 205.

Likewise, the second machine 140 selects the second clustered data set 225 and the second stochastic model 245. For example, because the second clustered data set 225 was already assigned to the second stochastic model 245 (block 241), the second machine 140 is only required to select one of the second clustered data set 225 and the second stochastic model 245 to select both since they are paired together. The second machine 140 generates, with the second stochastic model 245, a second synthetic data set 256 (block 255). The second synthetic data set 256 has generated data for each one of the plurality of attributes from the plurality of data sets 205. For example, the second synthetic data set 256 may include a second generated data record 257 and a plurality of additional second generated data records 258. Each of the second generated data record 257 and the plurality of additional second generated data records 258 has each one of the plurality of attributes from the plurality of data sets 205.

For example, to test a software application (e.g., an application for managing hospital medical records), the computer system running the software application may require test data (e.g., sample medical records). In the context of medical records, it may typically be preferable to generate the test data synthetically (e.g., due to the quantity of test data required, due to confidentiality concerns, etc.). Furthermore, multiple machines may generate synthetic data in parallel to save time, optimize computing resources, etc. By assigning individual stochastic models (e.g., first stochastic model 235 and second stochastic model 245) to individual data sets (e.g., first clustered data set 220 and second clustered data set 225), the two or more machines generate synthetic data simultaneously and in parallel while advantageously avoiding redundant synthetic data. For example, the second stochastic model 245 does not use the first clustered data set 220 when generating synthetic data because the first clustered data set 220 is assigned to the first stochastic model 235.

As an exemplary illustration, suppose that synthetic data generation method 200 is used to generate synthetic data in the form of medical records. The clustering module 110 receives a plurality of data sets 205 from the external data source 150 (block 210) (e.g., an external database). For example, the plurality of data sets 205 are individual patient medical records (e.g., 1,000 individual patient records) that have been scrubbed for testing purposes. Likewise, each data set (e.g., each individual patient record) of the plurality of data sets 205 includes a plurality of attributes. For example, each of the individual patient records includes a plurality of medical attributes. In an example, a first data set in the plurality of data sets 205 is the medical record for John Smith. John Smith's medical record includes the plurality of attributes, including age (e.g., 64 years old), sex (e.g., male), height (e.g., 6' 2"), weight (e.g., 210 lbs.), eye color (e.g., brown), blood type (e.g., O-positive), smoker status (e.g., non-smoker), cancer status (e.g., leukemia), and heart disease status (e.g., no heart disease).

Likewise, a second data set in the plurality of data sets 205 is the medical record for Jane Adams. Jane Adams' medical record includes the plurality of attributes, including age (e.g., 37 years old), sex (e.g., female), height (e.g., 5' 7"), weight (e.g., 145 lbs.), eye color (e.g., blue), blood type (e.g., B-positive), smoker status (e.g., non-smoker), cancer status (e.g., no cancer), and heart disease status (e.g., no heart disease). It should be noted that, while the plurality of attributes for Jane Adams' medical record are the same as those of John Smith's (e.g., both records have an age), the value of the attributes may be different (e.g., 64 years old vs. 37 years old) or may be the same (e.g., both are non-smokers). In other words, the value of the attributes for each data set (e.g., each medical record) is specific to each data set.

Likewise, a third data set in the plurality of data sets 205 is the medical record for Eugene Johnson. Eugene Johnson's medical record includes the plurality of attributes, including age (e.g., 74 years old), sex (e.g., male), height (e.g., 5' 10"), weight (e.g., 170 lbs.), eye color (e.g., hazel), blood type (e.g., AB-positive), smoker status (e.g., smoker), cancer status (e.g., lung cancer), and heart disease status (e.g., heart disease). It should be noted that, while the plurality of attributes for Eugene Johnson's medical record are the same as those of John Smith's and Jane Adams', the value of the attributes may be different or may be the same.

Likewise, a fourth data set in the plurality of data sets 205 is the medical record for Lisa Reynolds. Lisa Reynolds' medical record includes the plurality of attributes, including age (e.g., 53 years old), sex (e.g., female), height (e.g., 5' 2"), weight (e.g., 120 lbs.), eye color (e.g., brown), blood type (e.g., O-positive), smoker status (e.g., smoker), cancer status (e.g., no cancer), and heart disease status (e.g., heart disease). It should be noted that, while the plurality of attributes for Lisa Reynolds' medical record are the same as those of John Smith's, Jane Adams', and Eugene Johnson's, the value of the attributes may be different or may be the same.

The clustering module 110 partitions the plurality of data sets 205 (e.g., 1,000 individual patient records) into a plurality of clustered data sets (blocks 215 and 216). For example, the plurality of clustered data sets includes at least a first clustered data set 220 (e.g., 500 individual patient records) and a second clustered data set 225 (e.g., 500 individual patient records). Each data set from the plurality of data sets 205 is partitioned into one of the plurality of clustered data sets (e.g., every data set from the plurality of data sets 205 is partitioned into only one of the first clustered data set 220 or the second clustered data set 225). For example, the clustering module 110 partitions the first data set (e.g., John Smith's medical record), the second data set (e.g., Jane Adam's medical record), the fourth data set (e.g., Lisa Reynolds' medical record), along with a plurality of other data sets (e.g., 497 other individual patient records) from the plurality of data sets 205, into the first clustered data set 220. Likewise, for example, the clustering module 110 partitions the third data set (e.g., Eugene Johnson's medical record), along with a plurality of other data sets (e.g., 499 other individual patient records) from the plurality of data sets 205, into the second clustered data set 225.

The training module 120 assigns a respective stochastic model to each respective clustered data set of the plurality of clustered data sets. For example, the training module 120 receives the first clustered data set 220 (block 230). The training module 120 assigns a first stochastic model 235 (e.g., a first Markov model) to the first clustered data set 220 (block 231). Likewise, for example, the training module 120 receives the second clustered data set 225 (block 240). The training module 120 assigns a second stochastic model 245 (e.g., a second Markov model) to the second clustered data set 225 (block 241).

As an example, each of the first stochastic model and the second stochastic model are Markov models, which assume that future states are only dependent on the current state. For example, if data suggests that 30% of patients in a clustered data set (e.g., first clustered data set 220, second clustered data set 225, etc.) have cancer and 70% of patients are cancer free (e.g., the current state), a Markov model may dictate that a hypothetical patient (e.g., a future state) would have a 30% chance of having cancer. The probability of the current state dictates the future state. Likewise, for example, if data suggests that 27% of patients have blue eyes, 39% of patients have brown eyes, 13% of patients have green eyes, 21% of patients have hazel eyes (e.g., the current state), the Markov model may dictate that a hypothetical patient (e.g., a future state) would have a 21% chance of having hazel eyes.

Continuing on to FIG. 2B, the first machine 130 selects the first clustered data set 220 and the first stochastic model 235 (e.g., the first Markov model). The first machine 130 generates, with the first stochastic model 235 (e.g., the first Markov model), a first synthetic data set 251 (block 250). For example, the first machine 130 uses the first Markov model and information from the current state (e.g., information from the first clustered data set 220) including attributes (e.g., eye color) and statistical probability of attributes (e.g., 27% chance of having blue eyes, 39% chance of having brown eyes, 13% chance of having green eyes, 21% chance of having hazel eyes) to determine an eye color for Patient 1's medical record (e.g., green eyes). As an example, statistically, if there is a statistically significant quantity of patient medical records synthetically generated with this Markov model, one would expect approximately 13% of patients to have green eyes (given the probability noted above).

The Markov model described above is not just used for eye-color data generation (e.g., a single-attribute data generator); rather, the first machine 130 uses the first Markov model and information from the current state (e.g., information from the first clustered data set 220) including all of the attributes (e.g., age, sex, height, weight, eye color, blood type, smoker status, cancer status, and heart disease status) and statistical probability of each of the respective attributes to generate the first synthetic data set 251.

For example, the first synthetic data set 251 may include a first generated data record 252 (e.g., Patient 1's medical record). In an example, Patient 1's medical record includes the plurality of attributes including age (e.g., 68 years old), sex (e.g., male), height (e.g., 6' 0"), weight (e.g., 192 lbs.), eye color (e.g., brown), blood type (e.g., O-positive), smoker status (e.g., non-smoker), cancer status (e.g., liver cancer), and heart disease status (e.g., no heart disease). The first generated data record 252 (e.g., Patient 1's medical record) has each one of the plurality of attributes (e.g., age, sex, height, weight, eye color, blood type, smoker status, cancer status, and heart disease status) from the plurality of data sets 205 (e.g., the 1,000 individual patient records).

The first synthetic data set 251 may further include a plurality of additional first generated data records 253 (e.g., Patient 2's medical record, Patient 3's medical record, etc.). In an example, Patient 2's medical record includes the plurality of attributes including age (e.g., 27 years old), sex (e.g., female), height (e.g., 5' 4"), weight (e.g., 175 lbs.), eye color (e.g., hazel), blood type (e.g., B-positive), smoker status (e.g., non-smoker), cancer status (e.g., lung cancer), and heart disease status (e.g., no heart disease).

Each of the plurality of additional first generated data records 253 (e.g., Patient 2's medical record, Patient 3's medical record, etc.) may have each one of the plurality of attributes (e.g., age, sex, height, weight, eye color, blood type, smoker status, cancer status, and heart disease status) from the plurality of data sets 205. In an example, the first machine 130 uses the first Markov model and the first clustered data set 220 to generate 50,000 individual synthetic data records in the first synthetic data set 251 (e.g., Patient 1's medical record, Patient 2's medical record, Patient 3's medical record, up to Patient 50,000's medical record). It is important to note that each individual synthetic data record generated is not a copy of a data set in a clustered data set (e.g., the first clustered data set 220). For example, no individual synthetic data record is a copy of John Smith's medical record. Rather, each individual synthetic data record is a newly generated data record, created from a Markov model that is dynamically evaluating probability and is tied to a specific data cluster (e.g., the first clustered data set 220).

Likewise, the second machine 140 selects the second clustered data set 225 and the second stochastic model 245 (e.g., the second Markov model). The second machine 140 generates, with the second stochastic model 245 (e.g., the second Markov model), a second synthetic data set 256 (block 255). For example, the second machine 140 uses the second Markov model and information from the current state (e.g., information from the second clustered data set 225) including attributes (e.g., eye color) and statistical probability of attributes (e.g., 31% chance of having blue eyes, 42% chance of having brown eyes, 9% chance of having green eyes, 18% chance of having hazel eyes) to determine an eye color for Patient 501's medical record (e.g., brown eyes). As an example, statistically, if there is a statistically significant quantity of patient medical records synthetically generated with this Markov model, one would expect approximately 42% of patients to have brown eyes (given the probability noted above).

Also, while both the first Markov model and the second Markov model have the same attributes (e.g., eye color), a distinction between the first stochastic model 235 (e.g., the first Markov model) and the second stochastic model 245 (e.g., the second Markov model) is that the statistical probability of each attribute is determined by the data set (e.g., first clustered data set 220 and second clustered data set 225) respectively assigned to each Markov model. For example, the first Markov model has a statistical probability of 39% that a patient's eye color is brown, as dictated by the probability of attributes in the first clustered data set 220. By comparison, for example, the second Markov model has a statistical probability of 42% that a patient's eye color is brown, as dictated by the probability of attributes in the second clustered data set 225. Because each of the first Markov model and the second Markov model is assigned to a different unique clustered data set by the training module 120, each of the first Markov model and the second Markov model generates unique synthetic data.

As noted above, the second machine 140 generates, with the second stochastic model 245 (e.g., the second Markov model), the second synthetic data set 256 (block 255). For example, the second synthetic data set 256 may include a second generated data record 257 (e.g., Patient 50,001's medical record). In an example, Patient 50,001's medical record includes the plurality of attributes including age (e.g., 45 years old), sex (e.g., female), height (e.g., 5' 11"), weight (e.g., 140 lbs.), eye color (e.g., brown), blood type (e.g., O-negative), smoker status (e.g., smoker), cancer status (e.g., no cancer), and heart disease status (e.g., no heart disease). The second generated data record 256 (e.g., Patient 50,001's medical record) has each one of the plurality of attributes (e.g., age, sex, height, weight, eye color, blood type, smoker status, cancer status, and heart disease status) from the plurality of data sets 205 (e.g., the 1,000 individual patient records).

The second synthetic data set 256 may further include a plurality of additional second generated data records 258 (e.g., Patient 50,002's medical record, Patient 50,003's medical record, etc.). In an example, Patient 50,002's medical record includes the plurality of attributes including age (e.g., 19 years old), sex (e.g., female), height (e.g., 5' 3"), weight (e.g., 190 lbs.), eye color (e.g., green), blood type (e.g., A-positive), smoker status (e.g., smoker), cancer status (e.g., no cancer), and heart disease status (e.g., no heart disease).

The plurality of additional second generated data records 258 (e.g., Patient 50,002's medical record, Patient 50,003's medical record, etc.) has each one of the plurality of attributes (e.g., age, sex, height, weight, eye color, blood type, smoker status, cancer status, and heart disease status) from the plurality of data sets 205. In an example, the second machine 140 uses the second Markov model and the second clustered data set 225 to generate 50,000 individual synthetic data records in the second synthetic data set 256 (e.g., Patient 50,001's medical record, Patient 50,002's medical record, Patient 50,003's medical record, up to Patient 100,000's medical record).

In the example described above, the clustering module 110 partitions the plurality of data sets 205 (e.g., 1,000 individual patient records) into a plurality of clustered data sets (blocks 215 and 216) including the first clustered data set 220 (e.g., 500 individual patient records from the 1,000 individual patient records) and the second clustered data set 225 (e.g., a different 500 individual patient records from the 1,000 individual patient records). The first machine 130 uses the first Markov model and the first clustered data set 220 (e.g., 500 individual patient records from the 1,000 individual patient records) to generate one-hundred times as many synthetic records. For example, the first synthetic data set 251 includes 50,000 synthetic records (e.g., Patient 1's medical record, Patient 2's medical record, Patient 3's medical record, up to Patient 50,000's medical record). The second machine 140 uses the second Markov model and the second clustered data set 225 (e.g., 500 different individual patient records from the 1,000 individual patient records) to generate one-hundred times as many synthetic records. For example, the second synthetic data set 256 includes 50,000 synthetic records (e.g., Patient 50,001's medical record, Patient 50,002's medical record, Patient 50,003's medical record, up to Patient 100,000's medical record).

In another example, each of the first machine 130 and the second machine 140 generate more synthetic records. For example, the first machine 130 may use the first Markov model and the first clustered data set 220 (e.g., 500 individual patient records from the 1,000 individual patient records) to generate one-thousand times as many synthetic records. For example, the first synthetic data set 251 includes 500,000 synthetic records generated by the first machine 130. Likewise, for example, the second machine 140 may use the second Markov model and the second clustered data set 225 (e.g., 500 different individual patient records from the 1,000 individual patient records) to generate one-thousand times as many synthetic records. For example, the second synthetic data set 256 includes 500,000 synthetic records generated by the second machine 140. In this example, the total number of synthetic records generated is one million synthetic records. Moreover, because the first Markov model and the second Markov model are different (e.g., different probabilities of attributes, as dictated by the respective clustered data sets), the synthetic data sets they generate are unique. In another example, ten different machines may be used to share the processing of generating the one million synthetic records.

While the example above involves medical records, it should be appreciated that other types of records could be used in synthetic data generation method 200. For example, other types of records could include insurance records, employment records, manufacturing records, etc.

Figure 3:
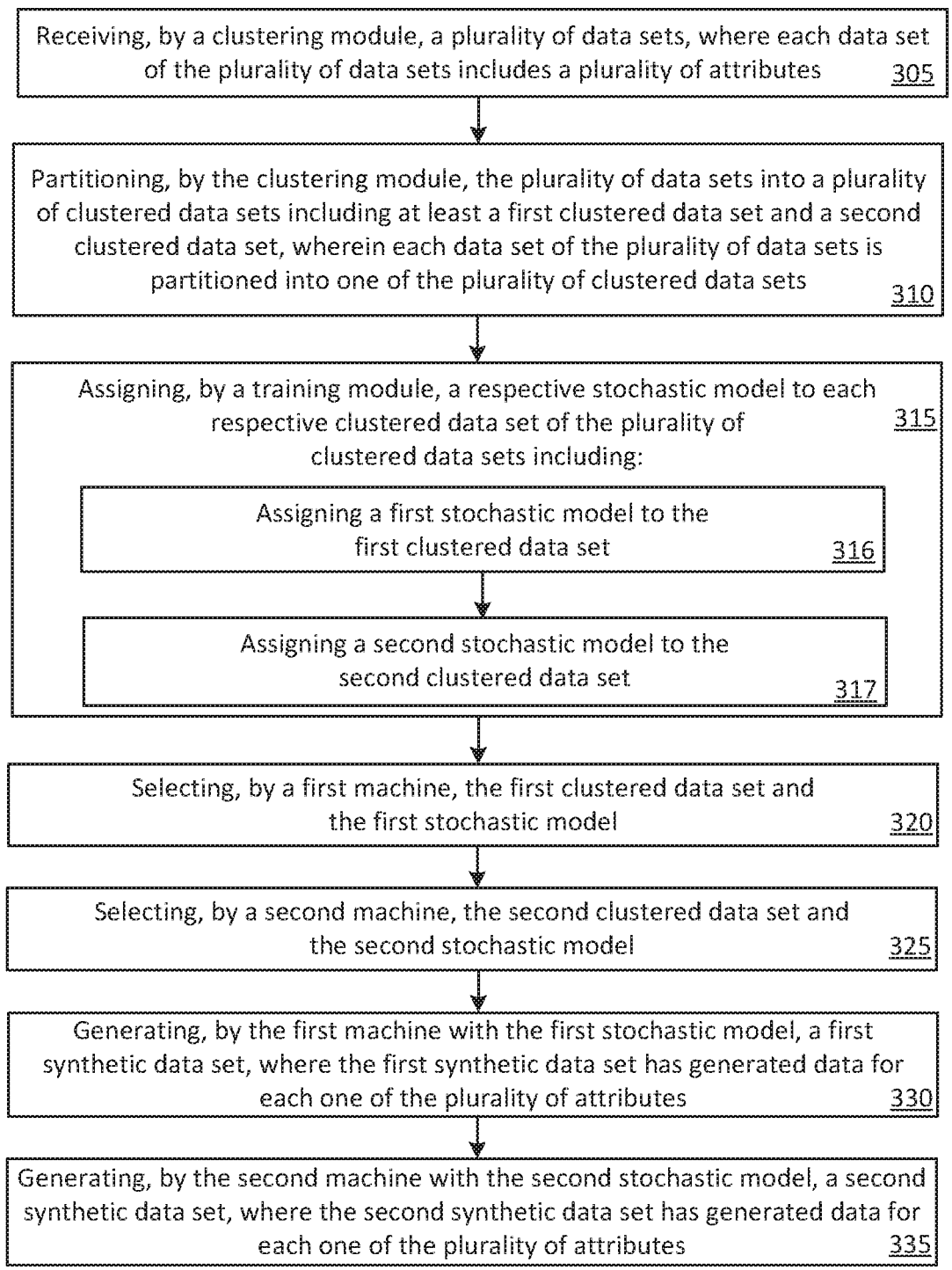
FIG. 3 is a flowchart illustrating an example method of synthetic data set generation according to an example embodiment of the present disclosure.

FIG. 3 is a flowchart illustrating an example method of synthetic data set generation according to an example embodiment of the present disclosure. Although the example method 300 is described with reference to the flowchart illustrated in FIG. 3, it will be appreciated that many other methods of performing the acts associated with the method may be used. For example, the order of some of the blocks may be changed, certain blocks may be combined with other blocks, and some of the blocks described are optional. The method may be performed by processing logic that may comprise hardware (e.g., circuitry, dedicated logic, etc.), software, or a combination of both.

The example method 300 begins with receiving, by a clustering module, a plurality of data sets (block 305). For example, the clustering module 110 receives the plurality of data sets 205 (e.g., received from the external data source 150). Each data set of the plurality of data sets includes a plurality of attributes. The example method 300 includes partitioning, by the clustering module, the plurality of data sets into a plurality of clustered data sets including at least a first clustered data set and a second clustered data set (block 310). For example, the clustering module 110 partitions the plurality of data sets 205 into the first clustered data set 220 and the second clustered data set 225. Each data set of the plurality of data sets is partitioned into one of the plurality of clustered data sets. For example, each of the plurality of data sets 205 is included in either the first clustered data set 220 or the second clustered data set 225 and each of the plurality of data sets 205 is only included in only one of the clustered data sets.

The example method 300 includes assigning, by a training module, a respective stochastic model to each respective clustered data set of the plurality of clustered data sets (block 315). This includes assigning a first stochastic model to the first clustered data set (block 316). For example, the training module 120 assigns the first stochastic model 235 to the first clustered data set 220. This also includes assigning a second stochastic model to the second clustered data set (block 317). For example, the training module 120 assigns the second stochastic model 245 to the second clustered data set 225.

The example method 300 includes selecting, by a first machine, the first clustered data set and the first stochastic model (block 320). For example, the first machine 130 selects the first stochastic model 235. This selection may necessarily include the first clustered data set 220, as the first clustered data set 220 has already been assigned to the first stochastic model 235 by the training module 120. The example method 300 includes selecting, by a second machine, the second clustered data set and the second stochastic model (block 325). For example, the second machine 140 selects the second stochastic model 245. This selection may necessarily include the second clustered data set 225, as the second clustered data set 225 has already been assigned to the second stochastic model 245 by the training module 120.

The example method 300 includes generating, by the first machine with the first stochastic model, a first synthetic data set (block 330). The first synthetic data set has generated data for each one of the plurality of attributes. For example, the first machine 130 uses the first stochastic model 235 and the first clustered data set 220 to generate the first synthetic data set 251. The example method 300 includes generating, by the second machine with the second stochastic model, a second synthetic data set (block 335). The second synthetic data set has generated data for each one of the plurality of attributes. For example, the second machine 140 uses the second stochastic model 245 and the second clustered data set 225 to generate the second synthetic data set 256.

Figure 4A:
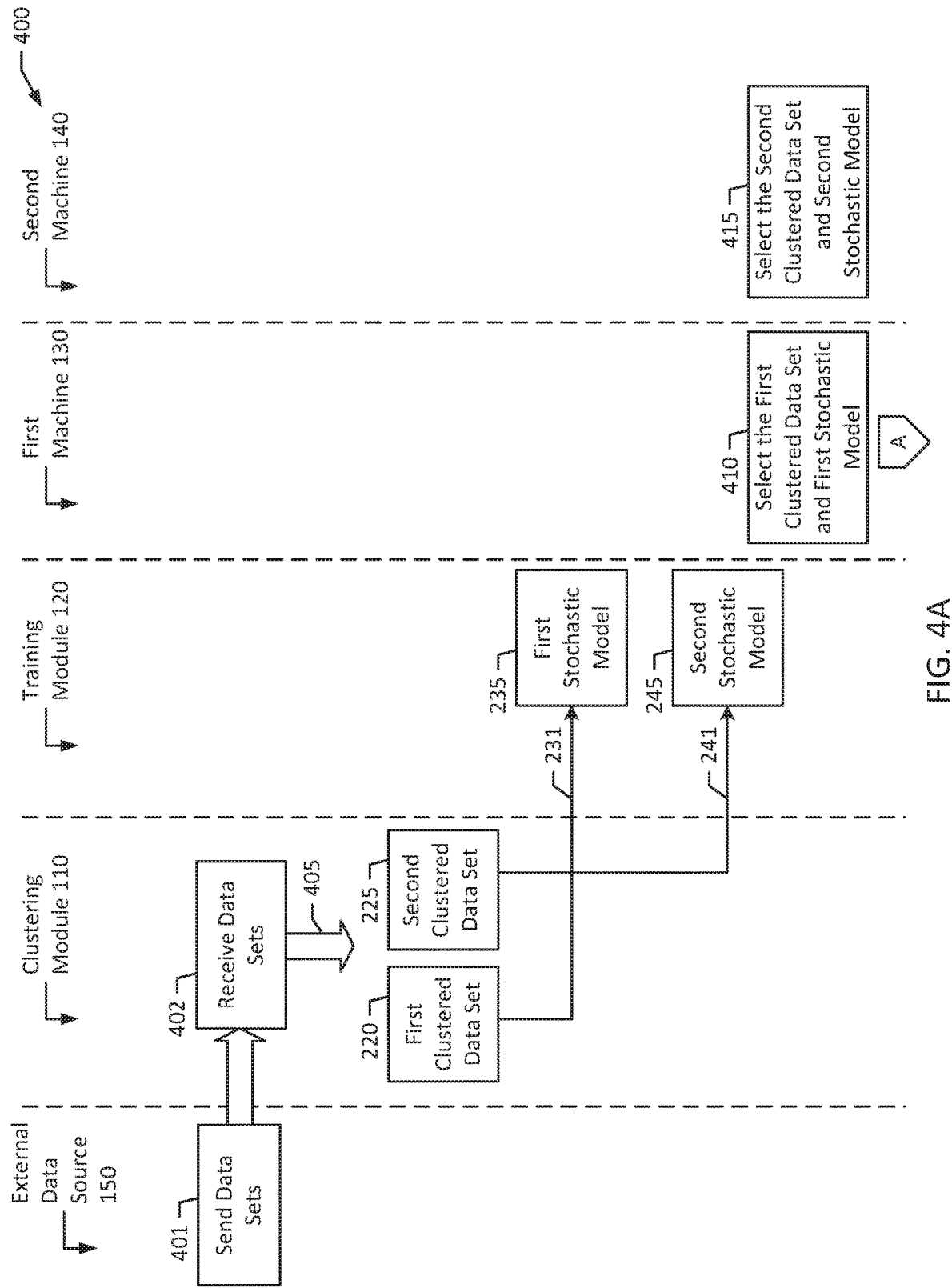
FIGS. 4A-4B are a flow diagram illustrating an example method of synthetic data set generation according to an example embodiment of the present disclosure.
Figure 4B:
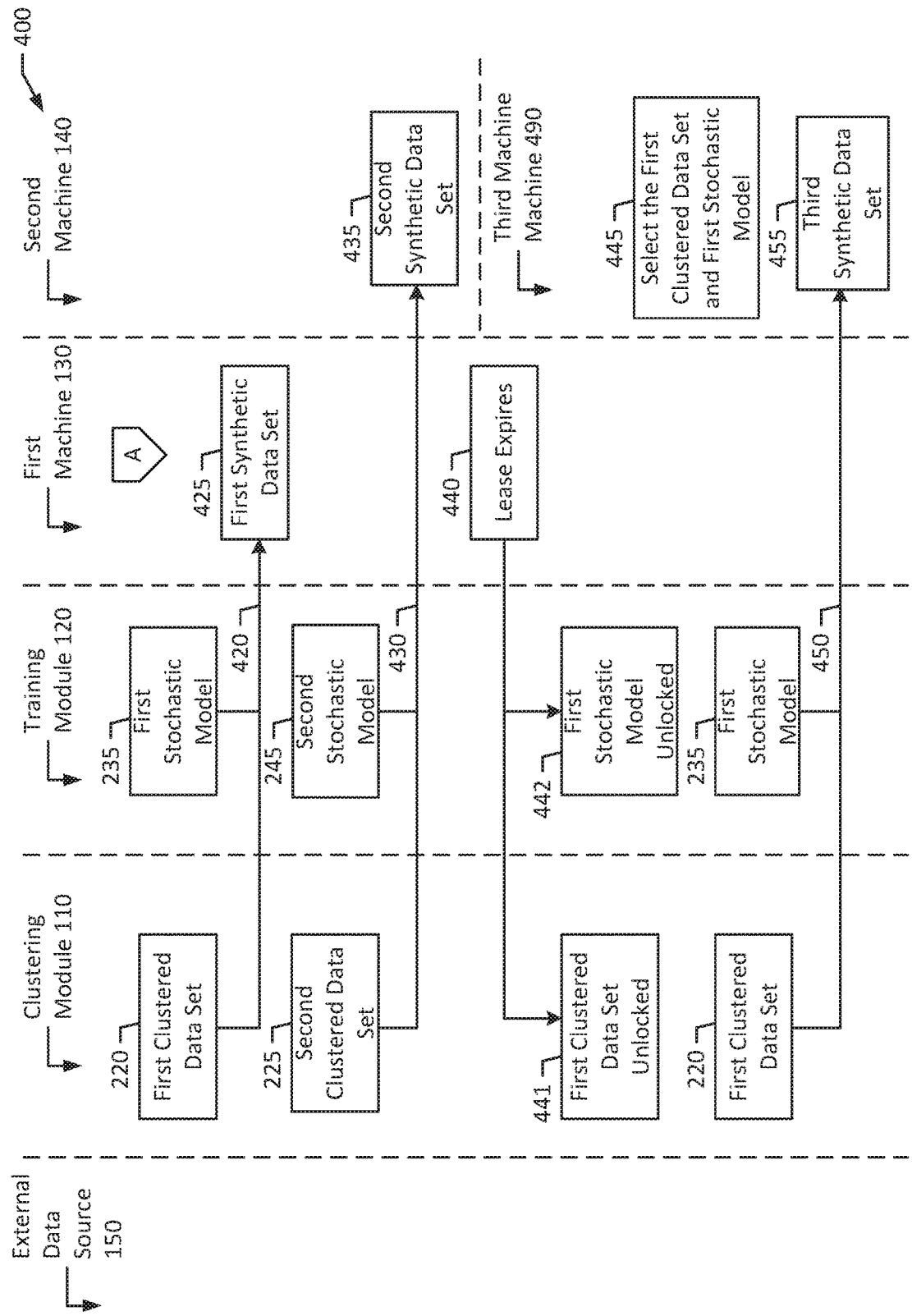

FIGS. 4A-4B are a flow diagram illustrating an example method of synthetic data set generation according to an example embodiment of the present disclosure. Although the example method 400 is described with reference to the flow diagram illustrated in FIGS. 4A-4B, it will be appreciated that many other methods of performing the acts associated with the method may be used. For example, the order of some of the blocks may be changed, certain blocks may be combined with other blocks, and some of the blocks described are optional. The method may be performed by processing logic that may comprise hardware (e.g., circuitry, dedicated logic, etc.), software, or a combination of both.

The example method 400 begins with the external data source 150 sending a plurality of data sets to a clustering module 110 (block 401). For example, the plurality of data sets are individual patient records. Likewise, for example, each data set in the plurality of data sets includes a plurality of attributes. The plurality of data sets are received by the clustering module (block 402).

The clustering module 110 partitions the plurality of data sets into a plurality of clustered data sets (block 405) including a first clustered data set 220 and a second clustered data set 225. For example, each data set from the plurality of data sets is partitioned into one of the plurality of clustered data sets (e.g., every data set from the plurality of data sets is partitioned into one of the first clustered data set 220 or the second clustered data set 225). The clustering module 110 may partition the plurality of data sets into any number of clustered data sets (e.g., two clustered data sets, nine clustered data sets, etc.). In an example, the clustering module 110 uses k-means clustering. For example, if k=3, the clustering module 110 partitions the plurality of data sets into three clustered data sets. In a different example, the clustering module 110 uses Markov Cluster (MCL) clustering. For example, the clustering module 110 dynamically approximates the ideal number of clustered data sets for the given plurality of data sets.

The training module 120 assigns a first stochastic model 235 to the first clustered data set 220 (block 231). Likewise, the training module 120 assigns a second stochastic model 245 to the second clustered data set 225 (block 241). In an example, the training module 120 creates each of the first stochastic model 235 and the second stochastic model 245. In an example, each of the first stochastic model 235 and the second stochastic model 245 are Markov models. For example, the first stochastic model 235 is a first Markov model. Likewise, for example, the second stochastic model 245 is a second Markov model. In a different example, each of the first stochastic model 235 and the second stochastic model 245 are other types of stochastic modeling processes that generate different statistical permutations (e.g., Bernoulli processes, Branching processes, Chinese restaurant processes, Galton-Watson processes, Moran processes, Random walk processes, etc.).

The first machine 130 selects the first clustered data set 220 and the first stochastic model 235 (block 410). In an example, responsive to the first machine 130 selecting the first clustered data set 220 and the first stochastic model 235, the first stochastic model 235 is locked out, such that the second machine 140 is unable to use the first stochastic model 235 to generate the second synthetic data set 435 (e.g., only one machine may use a stochastic model at a given time). For example, lockout of the first stochastic model 235 is performed by a fencing token. In an example, an indication of the first stochastic model's 235 locked out status is recorded in a data store (e.g., a strongly consistent data store). Also, in an example, upon selecting the first clustered data set 220 and the first stochastic model 235, the first machine 130 is granted a lease, which has an expiration time.

Continuing on with example method 400, the second machine 140 selects the second clustered data set 225 and the second stochastic model 245 (block 415). In an example, each of the first machine 130 and the second machine 140 are physical computers. For example, each of the first machine 130 and the second machine 140 are remotely located physical computers. For example, each of the first machine 130 and the second machine 140 are communicating with the clustering module 110 and training module 120 via the network 160 (e.g., a distributed system). In another example, each of the first machine 130 and the second machine 140 are virtual machines.

The first machine 130 generates, with the first stochastic model 235 and the first clustered data set 220, a first synthetic data set 425 (block 420). In an example, the first synthetic data set 425 includes a first generated data record and a plurality of additional first generated data records. Each of the first generated data record and the plurality of additional first generated data records has generated data for each of the plurality of attributes. The second machine 140 generates, with the second stochastic model 245 and the second clustered data set 225, a second synthetic data set 435 (block 430). In an example, the second synthetic data set 435 includes a second generated data record and a plurality of additional second generated data records. Each of the second generated data record and the plurality of additional second generated data records has generated data for each of the plurality of attributes.

It should be noted that the first machine 130 is not limited to the first clustered data set 220 and the first stochastic model 235. For example, when selecting a data set and stochastic model, the first machine 130 may alternatively select the second clustered data set 225 and the second stochastic model 245. In this example, the first machine 130 generates, with the second stochastic model 245 and the second clustered data set 225, the second synthetic data set 435.

In an example, the first synthetic data set 425 and the second synthetic data set 435 are simultaneously generated in parallel. For example, the first machine 130 generates, with the first stochastic model 235 and the first clustered data set 220, the first synthetic data set 425 (block 420) while the second machine 140 simultaneously generates, with the second stochastic model 245 and the second clustered data set 225, the second synthetic data set 435 (block 430) in parallel. Generating synthetic data in parallel allows for optimization of computing resources (e.g., multiple machines being used for data generation). In a related example, each respective stochastic model (e.g., the first stochastic model 235 and the second stochastic model 245) simultaneously generating data in parallel generates different classes of data, such that only one respective stochastic model generates each class of data at any point in time. For example, because the first clustered data set 220 is different from the second clustered data set 225, and the first stochastic model 235 is different from the second stochastic model 245, each of the first stochastic model 235 and the second stochastic model 245 are generating different classes of data (e.g., different synthetic data sets) simultaneously. In an example, each of the first synthetic data set 425 and the second synthetic data set 435 are highly orthogonal data sets (e.g., without intersection between the data sets).

In an example, once the first machine 130 generates the first synthetic data set 425 (block 420), the first synthetic data set 425 is fenced before passing to an external source (e.g., an external memory). In an example, if the fencing token is not currently active, the first synthetic data set 425 may be fenced from being passed to an external source. For example, if the lease has expired, the first synthetic data set 425 may be prevented from being sent to an external source. In a related example, if the fencing token is not currently active and has not been renewed, the first synthetic data set 425 is wiped. For example, if the lease has not been renewed, the first synthetic data set 425 is deleted. This may ensure, for example, that synthetic data sets are only generated and passed to external sources during periods that the lease is active.

Continuing on with example method 400, upon selecting the first clustered data set 220 and the first stochastic model 235 (block 410), the first machine 130 is granted the lease, which has an expiration time. For example, the expiration time may be one hour. Eventually, the lease expires on the first machine 130 (block 440). Responsive to the lease expiring at the expiration time, the first clustered data set 220 is unlocked (block 441) and the first stochastic model is unlocked (block 442).

Once unlocked, a third machine 490 may select the first clustered data set 220 and the first stochastic model 235 (block 445) to generate a third synthetic data set 455 (block 450).

In an example, each of the first synthetic data set 425, the second synthetic data set 435, and the third synthetic data set 455 are used for testing purposes (e.g., testing an application or a database). In a related example, testing of the database includes indexing of the database using each of the first synthetic data set 425, the second synthetic data set 435, and the third synthetic data set 455.

Figure 5:
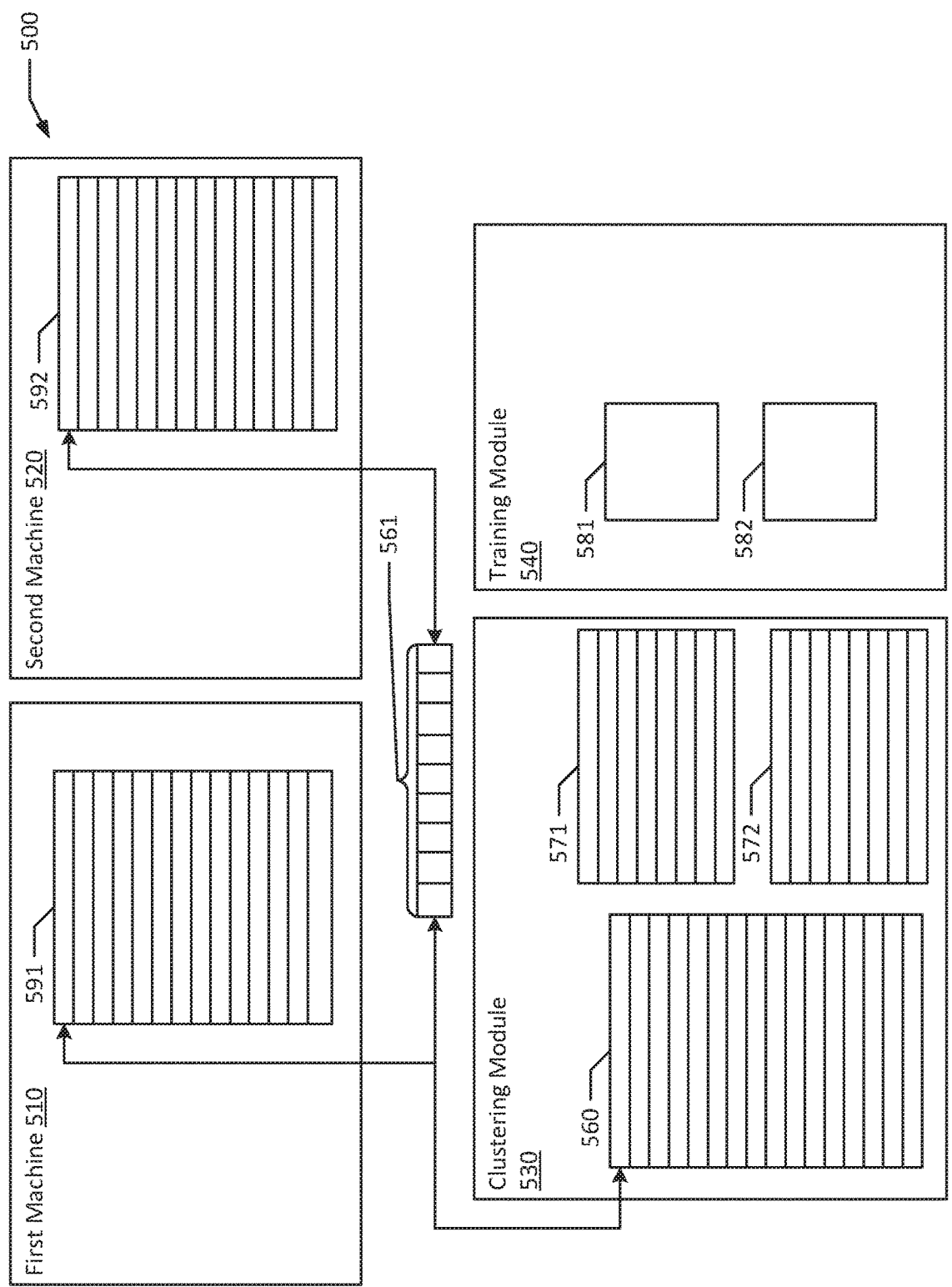
FIG. 5 is a block diagram of an exemplary system for generating synthetic data sets according to an example embodiment of the present disclosure.

FIG. 5 is a block diagram of an exemplary system for generating synthetic data sets according to an example embodiment of the present disclosure. The system 500 includes a first machine 510 and a second machine 520. The system 500 further includes a clustering module 530 and a training module 540.

The clustering module 530 includes a plurality of data sets 560. Each data set of the plurality of data sets 560 includes a plurality of attributes 561. The clustering module 530 partitions the plurality of data sets 560 into a plurality of clustered data sets including a first clustered data set 571 and a second clustered data set 572. Each data set of the plurality of data sets 560 is partitioned into one of the plurality of clustered data sets.

The training module 540 assigns a respective stochastic model to each respective clustered data set of the plurality of clustered data sets. For example, the training module 540 assigns a first stochastic model 581 to the first clustered data set 571. Likewise, the training module 540 assigns a second stochastic model 582 to the second clustered data set 572.

The first machine 510 selects the first clustered data set 571 and the first stochastic model 581. The first machine 510 generates, with the first stochastic model 581, a first synthetic data set 591. The first synthetic data set 591 has generated data for each one of the plurality of attributes 561. Likewise, the second machine 520 selects the second clustered data set 572 and the second stochastic model 582. The second machine 520 generates, with the second stochastic model 582, a second synthetic data set 592. The second synthetic data set 592 has generated data for each one of the plurality of attributes 561.

It will be appreciated that all of the disclosed methods and procedures described herein can be implemented using one or more computer programs or components. These components may be provided as a series of computer instructions on any conventional computer readable medium or machine readable medium, including volatile or non-volatile memory, such as RAM, ROM, flash memory, magnetic or optical disks, optical memory, or other storage media. The instructions may be provided as software or firmware, and/or may be implemented in whole or in part in hardware components such as ASICs, FPGAs, DSPs or any other similar devices. The instructions may be configured to be executed by one or more processors, which when executing the series of computer instructions, performs or facilitates the performance of all or part of the disclosed methods and procedures.

It should be understood that various changes and modifications to the example embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method comprising:
receiving, by a clustering module, a plurality of data sets, wherein each data set of the plurality of data sets includes a plurality of attributes;
partitioning, by the clustering module, the plurality of data sets into a plurality of clustered data sets including at least a first clustered data set and a second clustered data set, wherein each data set of the plurality of data sets is partitioned into one of the plurality of clustered data sets;
assigning, by a training module, a respective stochastic model to each respective clustered data set of the plurality of clustered data sets including:
assigning a first stochastic model to the first clustered data set, and
assigning a second stochastic model to the second clustered data set;
selecting, by a first machine including a first memory and one or more processors in communication with the first memory, the first clustered data set and the first stochastic model;
selecting, by a second machine that is different from the first machine, the second machine including a second memory and one or more processors in communication with the second memory, the second clustered data set and the second stochastic model;
generating, by the first machine with the first stochastic model, a first synthetic data set, wherein the first synthetic data set has generated data for each one of the plurality of attributes;
generating, by the second machine with the second stochastic model, a second synthetic data set, wherein the second synthetic data set has generated data for each one of the plurality of attributes; and
testing at least one of an application and a database using each of the first synthetic data set and the second synthetic data set.

2. The method of claim 1, wherein, responsive to the first machine selecting the first clustered data set and the first stochastic model, the first stochastic model is locked out, such that the second machine is unable to use the first stochastic model to generate the second synthetic data set.

3. The method of claim 2, wherein lockout of the first stochastic model is performed by a fencing token.

4. The method of claim 2, wherein an indication of the first stochastic model's locked out status is recorded in a data store.

5. The method of claim 2, wherein upon selecting the first clustered data set and the first stochastic model, the first machine is granted a lease, wherein the lease has an expiration time.

6. The method of claim 5, wherein responsive to the lease expiring at the expiration time, the first stochastic model is unlocked, such that the first stochastic model may be selected by a third machine to generate a third synthetic data set.

7. The method of claim 1, wherein the training module creates the first stochastic model and the second stochastic model.

8. The method of claim 1, wherein each of the first stochastic model and the second stochastic model are Markov models.

9. The method of claim 1, wherein the first synthetic data set and the second synthetic data set are simultaneously generated in parallel.

10. The method of claim 9, wherein each respective stochastic model simultaneously generating data in parallel generates different classes of data, such that only one respective stochastic model generates each class of data at any point in time.

11. The method of claim 1, wherein each of the first machine and the second machine are remotely located physical computers.

12. The method of claim 1, wherein each of the first machine and the second machine are virtual machines.

13. The method of claim 1, wherein testing of the database includes indexing of the database using each of the first synthetic data set and the second synthetic data set.

14. A system comprising:
a first machine including a first memory and one or more processors in communication with the first memory;
a second machine that is different from the first machine, the second machine including a second memory and one or more processors in communication with the second memory;
a clustering module, wherein the clustering module:
receives a plurality of data sets, wherein each data set of the plurality of data sets includes a plurality of attributes; and
partitions the plurality of data sets into a plurality of clustered data sets including at least a first clustered data set and a second clustered data set, wherein each data set of the plurality of data sets is partitioned into one of the plurality of clustered data sets; and
a training module, wherein the training module:
assigns a respective stochastic model to each respective clustered data set of the plurality of clustered data sets including:
assigning a first stochastic model to the first clustered data set, and
assigning a second stochastic model to the second clustered data set;
wherein the first machine:
selects the first clustered data set and the first stochastic model; and
generates, with the first stochastic model, a first synthetic data set, wherein the first synthetic data set has generated data for each one of the plurality of attributes; and
wherein the second machine:
selects the second clustered data set and the second stochastic model; and
generates, with the second stochastic model, a second synthetic data set, wherein the second synthetic data set has generated data for each one of the plurality of attributes,
such that at least one of an application and a database is tested using each of the first synthetic data set and the second synthetic data set.

15. The system of claim 14, wherein, responsive to the first machine selecting the first clustered data set and the first stochastic model, the first stochastic model is locked out, such that the second machine is unable to use the first stochastic model to generate the second synthetic data set.

16. The system of claim 15, wherein upon selecting the first clustered data set and the first stochastic model, the first machine is granted a lease, wherein the lease has an expiration time.

17. The system of claim 16, wherein responsive to the lease expiring at the expiration time, the first stochastic model is unlocked, such that the first stochastic model may be selected by a third machine to generate a third synthetic data set.

18. The system of claim 14, wherein each of the first stochastic model and the second stochastic model are Markov models.

19. A computer readable non-transitory storage medium comprising executable instructions that, when executed, cause a clustering module to:
    receive a plurality of data sets, wherein each data set of the plurality of data sets includes a plurality of attributes; and
    partition the plurality of data sets into a plurality of clustered data sets including at least a first clustered data set and a second clustered data set, wherein each data set of the plurality of data sets is partitioned into one of the plurality of clustered data sets;
a training module to:
    assign a respective stochastic model to each respective clustered data set of the plurality of clustered data sets including:
        assigning a first stochastic model to the first clustered data set, and
        assigning a second stochastic model to the second clustered data set;
a first machine including a first memory and one or more processors in communication with the first memory to:
    select the first clustered data set and the first stochastic model; and
    generate, with the first stochastic model, a first synthetic data set, wherein the first synthetic data set has generated data for each one of the plurality of attributes; and
a second machine that is different from the first machine, the second machine including a first memory and one or more processors in communication with the first memory to:
    select the second clustered data set and the second stochastic model; and
    generate, with the second stochastic model, a second synthetic data set, wherein the second synthetic data set has generated data for each one of the plurality of attributes,
such that at least one of an application and a database is tested using each of the first synthetic data set and the second synthetic data set.

\* \* \* \* \*